(12) United States Patent
Bai

(10) Patent No.: US 9,586,013 B2
(45) Date of Patent: Mar. 7, 2017

(54) SELF-DESTRUCTING SYRINGE WITH HIGH LEVEL OF SAFETY AND CONVENIENT ASSEMBLY

(75) Inventor: Baodong Bai, Tianchang (CN)

(73) Assignee: Baodong Bai, Tianchang (CN)

( * ) Notice: Subject to any disclaimer, the term of this patent is extended or adjusted under 35 U.S.C. 154(b) by 291 days.

(21) Appl. No.: 14/131,187

(22) PCT Filed: Nov. 17, 2011

(86) PCT No.: PCT/CN2011/082337
§ 371 (c)(1),
(2), (4) Date: Jan. 6, 2014

(87) PCT Pub. No.: WO2013/056485
PCT Pub. Date: Apr. 25, 2013

(65) Prior Publication Data
US 2014/0221923 A1    Aug. 7, 2014

(30) Foreign Application Priority Data
Oct. 20, 2011    (CN) .......................... 2011 1 0320499

(51) Int. Cl.
*A61M 5/50* (2006.01)
*A61M 5/32* (2006.01)

(52) U.S. Cl.
CPC ........ *A61M 5/5066* (2013.01); *A61M 5/3202* (2013.01); *A61M 5/3221* (2013.01); *A61M 5/3234* (2013.01); *A61M 5/50* (2013.01); *A61M 2005/323* (2013.01); *A61M 2005/5073* (2013.01)

(58) Field of Classification Search
CPC .... A61M 2005/323; A61M 2005/5073; A61M 5/3202; A61M 5/3221; A61M 5/3234; A61M 5/50; A61M 5/5066
See application file for complete search history.

(56) References Cited

U.S. PATENT DOCUMENTS

| 6,752,784 | B2 | 6/2004 | Tsai |
| 2004/0049160 | A1 | 3/2004 | Hsieh et al. |
| 2012/0071826 | A1 | 3/2012 | Feng et al. |

FOREIGN PATENT DOCUMENTS

| CN | 2659464 Y | 12/2004 |
| CN | 2710665 Y | 7/2005 |
| CN | 1911467 A | 2/2007 |
| CN | 201469833 U | 5/2010 |
| CN | 101927048 A | 12/2010 |
| CN | 2017035029 U | 2/2011 |
| CN | 202236714 U | 5/2012 |

*Primary Examiner* — Imani Hayman
(74) *Attorney, Agent, or Firm* — Maschoff Brennan

(57) ABSTRACT

Disclosed is a self-destructing syringe, comprising an outer casing, a core bar, a piston, a conical head component, a syringe needle and a protecting jacket. The syringe needle is fixed in the conical head component, and the conical head component consists of a threaded conical head, a sealing ring, a transition part and a hollow wedge. The protecting jacket is put around the syringe needle and is movably connected to the needle base of the syringe needle; the conical head component is fixed in the inner cavity at the front end of the outer casing; the piston is installed on the core bar; the main part of the core bar is sheathed inside the outer casing; and the front end of the core bar is inserted into the conical head component and is able to make the syringe needle return inside the outer casing.

10 Claims, 15 Drawing Sheets

US 9,586,013 B2

SELF-DESTRUCTING SYRINGE WITH HIGH LEVEL OF SAFETY AND CONVENIENT ASSEMBLY

CROSS-REFERENCE TO RELATED APPLICATIONS

The present application is the national phase of International Application No. PCT/CN2011/082337, titled "SELF-DESTRUCTING SYRINGE WITH HIGH LEVEL OF SAFETY AND CONVENIENT ASSEMBLY", filed on Nov. 17, 2011, which claims the benefit of priority to Chinese patent application No. 201110320499.0 titled "SELF-DESTRUCTING SYRINGE WITH HIGH LEVEL OF SAFETY AND CONVENIENT ASSEMBLY", filed with the Chinese State Intellectual Property Office on Oct. 20, 2011, both of which applications are incorporated herein in their entireties by this reference.

TECHNICAL FIELD

The present application relates to a medical instrument, in particular to a disposable syringe, and in more particular to an easily assembled and highly safe self-destructive syringe.

BACKGROUND

A disposable sterilized syringe is a new medical instrument introduced to China in 1980s, which may avoid cross-infection and is easy to use, thus is very popular with doctors and patients. However, due to mismanagement of some medical institutions or interest drive, the disposable syringe is recycled, resold and reused. The reuse of the syringe causes the transmission of diseases, such as hepatitis B and acquired immune deficiency syndrome (AIDS).

In recent years, as indicated by some experts, the danger level of the medical staff suffered the occupational infection depends on the prevalence rate of the blood-borne disease among people. China is one of the countries having high incidence of hepatitis B, the number of the hepatitis B carriers is about 120 million, the infection rate of hepatitis C is up to 1.7%, and the prevalence of AIDS in China has already entered the period of rapid growth. Therefore, the medical staff in China is facing serious occupational exposure danger. Based on the results of questionnaire survey in 13 hospitals in Beijing, 1111 needles stabs occur to 432 probationer nurses in 10 months, i.e., it is 2.6 times per nurse per month in average, and due to the accidental injury, some nurses have been infected by blood-borne diseases, such as hepatitis B and AIDS.

For using the disposable syringe safely, and completely solving the cross-infection and the occupational exposure of the medical staff caused by the reuse of the disposable syringe, at the end of the last century, the World Health Organization (WHO) has proposed concepts such as safe injection, harmless to people being injected, and no risk to the medical-care staff. China has dedicated to develop and popularize the safe self-destructive syringe since 2000.

A good utility model or an invention should have the following advantages, such as having a low manufacturing accuracy, being easy to manufacture, being suitable for automated machine assembly, having a stable quality control in mass production. The safe self-destructive syringe that is commercial available presently has the following disadvantages.

A component of a retraction assembly (corresponding to a "conical connector assembly") for cooperating with an inner wall of a front end of a barrel to locate the retraction assembly is mostly designed as an integral loop structure or a small supporting jaw, the loop structure has a small expanding angle and the supporting jaw has a small body force, both of which may cause a low firmness of the location between the retraction assembly and the inner wall of the front end of the barrel, thereby causing a risk of the self-retraction of the retraction assembly during the injection process.

The retraction assembly has no shockproof design, thus the shock during the long-distance transportation may also cause the risk of the self-retraction of the retraction assembly.

The head of the barrel has no member for preventing the retraction assembly from being overly pushed forward or has too small force to prevent the retraction assembly from being pushed forward, such that in practical assembly process, the retraction assembly may be pushed out of the opening at the head of the barrel due to an excessive assembly force, thereby causing assembly problem.

In the retraction assembly, a conical connector, for assembling a syringe needle, and a structural member, for cooperating with the inner wall of the front end of the barrel to locate the retraction assembly, are formed integrally, and the locating structure is designed as a small supporting jaw. So that, firstly, a mould manufacturing accuracy is too high, the manufacture is difficult and the product fraction defective is high, and secondly, each mould has less cavities (for an injection machine of 180 tons, each mould can only produce 32 parts), thus the mass production is not suitable.

There is no sealing ring provided between the retraction assembly and the inner wall of the barrel, which may cause the leakage problem; or the sealing ring is provided, however due to the complicated design structure of the retraction assembly, the assembly of the sealing ring is difficult, thereby causing the conventional syringe having a low adaptability for automation and being not suitable for mass production with the automatic assembling machine.

The design of the retraction mechanism also has disadvantages. The conventional retraction mechanism mostly uses a three or more sequential retractions, which are formed in this way, the retracting force of the plunger is transmitted to a corresponding part, and then is transmitted to another corresponding part or to more corresponding parts via the first corresponding part, thus may cause a risk of unstable retraction operation.

Further, mostly there is no retraction restricting mechanism in the inner wall of the rear end of the barrel, such that if the medical staff operates carelessly, the needle tip may be retracted excessively to be pulled out, which may cause other accidents.

Due to above disadvantages, presently the safe self-destructive syringe has not been rapidly and widely used in China yet. Therefore, it is important to provide an easily manufactured and highly safe disposable syringe for improving the medical safety of China.

SUMMARY

An object of the present application is to provide a highly safe self-destructive syringe, which has a low manufacturing accuracy, is easy to assemble, has a high adaptability for automation, and is suitable for mass production, so as to solve problems of the existing disposable safe self-destructive syringe caused by unreasonable structural design, such as being not easy to manufacture and assemble, hard to adapt to the mass production, having a low qualified rate and a potential safety hazard during the self-destruction process.

A technical solution of the present application is as follow.

An easily assembled and highly safe self-destructive syringe includes a barrel 1, a plunger 2, a piston 3, a conical connector assembly 8, a syringe needle 9 and a protective cap 10. The syringe needle 9 is mounted in the conical connector assembly 8, the protective cap 10 is mounted above the syringe needle 9 to cover the syringe needle 9 and is movably connected to a needle seat of the syringe needle 9, the conical connector assembly 8 is mounted in an inner cavity of a front end of the barrel 1, the piston 3 is mounted on the plunger 2, a main body portion of the plunger 2 is mounted in the barrel 1, and a front end of the plunger 2 is configured to insert into the conical connector assembly 8 during the injection operation and drive the syringe needle 9 mounted on the conical connector assembly 8 to retract into the barrel 1. The conical connector assembly 8 includes a thread conical connector 4, a sealing ring 5, a transition part 6 and a hollow wedge 7. A lower portion of the thread conical connector 4 is inserted into an annular groove 621 and an annular recess 63 of the transition part 6, and the sealing ring 5 is press fitted among joint surfaces of the thread conical connector 4, the transition part 6 and an inner cavity wall surface of the front end of the barrel 1. The hollow wedge 7 is insertedly mounted in the transition part 6 and expands a blade 64 at a lower part of the transition part 6 via two annular inclined steps 73 on the hollow wedge 7, so as to locate the conical connector assembly 8 in the inner cavity of the front end of the barrel 1.

The hollow wedge 7 is of a hollow structure, and an upper portion of the hollow wedge 7 is a hollow cylinder 71. Four elastic retaining teeth 72 protruding inwardly and upwardly are uniformly distributed along a circumference at an inner cavity opening of an end surface of a head portion of the hollow cylinder 71. An annular groove 711 is provided on an outer wall surface of the cylinder 71, and the two annular inclined steps 73 inclining outwardly and downwardly are provided on an outer side of a lower portion of the cylinder 71. The transition part 6 is of a hollow structure, and an outer connecting body 61 and an inner connecting body 62 are provided on an upper portion of the transition part 6. The inner connecting body 62 is hollow, the annular recess 63 is formed between the outer connecting body 61 and the inner connecting body 62, and the annular groove 621 in communication with the recess 63 is provided on an outer wall surface of the inner connecting body 62. Six spaced identical blades 64, extending downward from an outer wall surface of the outer connecting body 61, are provided at a lower portion of the transition part 6 and are uniformly distributed on a same circumference. A bottom surface of each blade 64 is a sloping surface, a groove 641 is provided in an inner wall surface of each blade 64 to form a fragile portion of the blade so as to facilitate the outward expanding of the blades being pushed. A big inwardly protruding portion 643 corresponding to the inclined step 73 of the hollow wedge 7 and a small inwardly protruding portion 642 corresponding to an annular groove 711 of the hollow wedge 7 are provided in the inner wall surface of each blade 64, and the small inwardly protruding portion 642 is fitted in the annular groove 711 for preventing the shock during the product transportation.

A first annular flange 11 is provided on an inner wall at an end surface of a head portion of the barrel 1 for restricting the assembled conical connector assembly 8 from being pushed forward, and a second annular flange 12 is provided on the inner wall below the first annular flange 11 for restricting the assembled conical connector assembly 8 from being retracted. A retaining annular groove 13 and an annular protruding portion 14 are provided on an inner wall of a rear end of the barrel 1, several longitudinal strip inwardly protruding ribs 15 are distributed uniformly on the inner wall of the barrel 1 below the first annular flange 11, all the strip inwardly protruding ribs 15 are starting at a same circumference at a root portion of a bottom surface of the first annular flange 11 and have the same length, and an inwardly protruding height of the inwardly protruding ribs 15 is lower than an inwardly protruding height of the first annular flange 11.

A first retaining member 21 corresponding to the retaining annular groove 13 at the rear end of the barrel 1 and a second retaining member 22 corresponding to the annular protruding portion 14 at the rear end of the barrel 1 are provided on the plunger 2. The first retaining member 21 includes four arc sheets provided on a same circumference, a thickness side of the first retaining member 21 is tangent to a circumference of a bottom surface of the first retaining member 21, and forms a chamfer angle with a circumference of a top surface of the first retaining member 21, such that the first retaining member 21 can smoothly pass through the retaining annular groove 13 in the inner wall of the rear end of the barrel 1 when the plunger 2 is moving forward in the inner cavity of the barrel 1, but can not pass through the retaining annular groove 13 when the plunger 2 is moving backward. The second retaining member 22 is an integral circle retaining member coaxial with the plunger 2, a circumference diameter of the second retaining member 22 is slightly less than a circumference diameter of the first retaining member 21 and is slightly larger than a diameter of the inner cavity of the barrel 1 at the annular protruding portion 14, and a thickness side of the second retaining member 22 also is tangent to a circumference of a bottom surface of the second retaining member 22, and forms a chamfer angle with a circumference of a top surface of the second retaining member 22. A reinforcing rib 23 is provided on the plunger 2 below the first retaining member 21, a fragile portion 24 is provided on the plunger 2 below the reinforcing rib 23, a first tapered boss 25 and a second tapered boss 26 are provided at a head portion of the plunger 2 sequentially along an axis, a circumference diameter of a bottom surface of the first tapered boss 25 is less than a circumference diameter of a bottom surface of the second tapered boss 26, and a slip-resistant rib 28 is provided on a bottom surface of a pushing portion 27 of the plunger 2.

An upper portion 41 of the thread conical connector 4 is a standard Luer locking conical connector which can cooperate with various standard syringe needles. Four elastic retaining teeth 412 are provided on an inner cavity wall surface of a conical connector hole 411 along a same circumference, several strip outwardly protruding ribs 413 are distributed uniformly on an outer surface of the upper portion 41 of the thread conical connector 4, and all the outwardly protruding ribs 413 are starting at a same circumference and have the same length. An outwardly protruding height of the strip outwardly protruding ribs 413 of the thread conical connector 4 is equal to an inwardly protruding height of the strip inwardly protruding ribs 15 of the barrel 1. An end portion of the upper portion 41 of the thread conical connector 4 has an outer diameter larger than a diameter of the inner cavity of the barrel 1 at the first annular flange 11, and has an inner diameter equal to or less than a diameter of the inner cavity of the barrel 1 at the first annular flange 11. A lower portion 42 of the thread conical connector 4 is a hollow cylinder, and an annular inward flange 421 is provided on a wall surface of an inner cavity of the lower portion 42 of the thread conical connector 4.

The circumference diameter of the bottom surface of the first tapered boss 25 at the head portion of the plunger 1 is less than a diameter of a circle formed by a top inner wall of the elastic retaining teeth 72, in a natural state, at the head portion of the hollow wedge 7, and is larger than a diameter of a circle formed by a top inner wall of the elastic retaining teeth 412, in a natural state, in an inner cavity of the thread conical connector 4. The circumference diameter of the bottom surface of the second tapered boss 26 at the head portion of the plunger 2 is larger than the diameter of the circle formed by the top inner wall of the elastic retaining teeth 72, in a natural state, at the head portion of the hollow wedge 7.

The strip outwardly protruding ribs 413, distributed uniformly on the outer wall surface of the thread conical connector 4, cooperate with the strip inwardly protruding ribs 15, provided on the inner wall of the barrel 1 below the first annular flange 11, so as to ensure that the conical connector assembly 8 can not rotate, and meanwhile the conical connector assembly and the inner wall of the barrel 1 form an interference fit via the sealing ring 5 so as to achieve the sealing.

A distance from the bottom surface of the second tapered boss 26 at the front end of the plunger 2 to the bottom surface of the first tapered boss 25 is larger than a distance from a top surface of the elastic retaining teeth 72 of the hollow wedge 7 to a top surface of the elastic retaining teeth 412 in the inner cavity of the thread conical connector 4 in an assembled conical connector assembly, and the distance difference is enough for the second tapered boss 26 to retract the hollow wedge 7 until the restriction to blades 64 of the transition part 6 from the hollow wedge 7 is removed after the liquid medicine injection is finished. The first tapered boss 25 at the head portion of the plunger corresponds to the elastic retaining teeth 413 in the thread conical connector 4, and the second tapered boss 26 corresponds to the elastic retaining teeth 72 at the head portion of the hollow wedge 7. When the plunger 2 moves forward in the inner cavity of the barrel 1, the bosses 25 and 26 and the elastic retaining teeth 72 and 412 form a forward tooth shape, thus the plunger 2 can pass through successfully, and when the plunger 2 is retracted, the bosses 25 and 26 and the elastic retaining teeth 72 and 412 form a reversed tooth shape.

When the injection of predetermined liquid medicine in the syringe is finished, a head of the plunger 2 at the front end of the piston 3 is extended to the front of the elastic retaining teeth 412 in the inner cavity of the thread conical connector 4, so as to effectively reduce a residual amount of the liquid medicine. Meanwhile, when the liquid medicine injection is finished, the plunger 2 is retracted, firstly, the second tapered boss 26 hooks the elastic retaining teeth 72 at the head portion of the hollow wedge 7 to retract it, such that the restriction to the blades 64 of the transition part 6 from the hollow wedge 7 is removed. When the transition part 6 is not restricted by the hollow wedge 7, the outwardly expanded blades 64 of the transition part 6 return to an original state, thereby breaking away from the restriction from the second annular flange 12 on the inner wall of the barrel 1. Meanwhile the first tapered boss 25 at the head portion of the plunger 2 hooks the elastic retaining teeth 412 in the inner cavity of the thread conical connector 4 and pulls back the conical connector assembly so as to retract the syringe needle into the barrel 1, until the first retaining member 21 of the plunger 2 slides into the retaining annular groove 13 on the inner wall of the rear end of the barrel 1.

Meanwhile the second retaining member 22 is resisted by the annular protruding portion 14 on the inner wall of the rear end of the barrel 1, such that the retraction-stopping force on the plunger 2 becomes larger, in this situation when pulling hard the plunger 2, the plunger 2 is broken due to the fragile portion 24 provided on the plunger 2, thereby achieving the self-destruction function of the syringe and the security protection function of the syringe needle.

Advantageous effects of the present application are as follows.

In the conical connector assembly, the thread conical connector, for assembling the syringe needle, and a structural member (i.e., the transition part), for cooperating with the inner wall of the front end of the barrel so as to locate the conical connector assembly, are designed as separate parts, such that the conical connector assembly has a simple structure, may facilitate the mould manufacture, and each mould can be designed as one hundred and eight cavities (i.e., for an injection molding machine of one hundred and eighty tons, each mould can produces one hundred and eight parts), thus the production efficiency is improved significantly. Meanwhile due to the separate structural design of the thread conical connector and the transition part, the sealing ring, assembled between the thread conical connector and the transition part for ensuring the sealing performance, is much easier to assemble (there is no need to enlarge a diameter of the sealing ring for assembling, which reduces the most difficult process), and is more suitable for assembling by an automatic assembling machine.

The provided transition part has a low manufacturing accuracy and is easy to machine, the transition part is designed as six (at least more than three) spaced large blades, which are easy to expand outward and return to an original state, thereby ensuring the firmness of the fitting between the conical connector assembly and the inner wall of the barrel and ensuring the effect of the retraction performance.

A retraction design, having a stable operation performance, is provided. After the liquid medicine injection is finished, the plunger directly retracts the conical connector assembly and the syringe needle into the barrel, thereby changing the unstable design in the current market, which includes three or more movable sequential retractions.

A member for preventing the assembled conical connector assembly from being overly pushed forward (such as the first annular flange) is provided on the inner wall of the head portion of the barrel.

A transportation shockproof design is improved in the fitting between the conical connector assembly and the inner wall of the barrel.

The retraction is safe. A retraction limiting mechanism for preventing the overly retraction of the plunger is provided at the inner wall of the rear end of the barrel. When the injection of the predetermined liquid medicine is finished, two bosses at the front end of the plunger respectively automatically slide into the retaining portions of two elastic retaining teeth for achieving the self-destruction, then the plunger is retracted manually to retract the used syringe needle into the inner cavity of the barrel together with the conical connector assembly, until the plunger falls into the retraction limiting mechanism, so as to ensure that the needle tip is locked inside the inner cavity of the barrel and will not be exposed, thereby effectively preventing the medical staff from being stabbed unintentionally and avoiding the risk of the syringe being reused.

The Luer thread conical connector can fit with various standard syringe needles and may form a tight and fixed fitting. The plunger at the front end of the piston is configured with an enough length, so as to ensure a less residual of the liquid medicine, thereby reducing the damage to the society caused by the waste after the injection.

For the integral design, the present application has a simple structure, a low mould manufacturing accuracy, is easy to machine, thus is more suitable for automatic assembly, and may facilitate the control of the quality stability of mass production and satisfy the market requirement, and meanwhile may avoid the risk of failure of the self-destruction performance caused by careless assembly or operation.

The operation is safe. The sharp needle tip is protected securely, thus the following refuse treatment operation is safe and reliable.

BRIEF DESCRIPTION OF THE DRAWINGS

FIG. 2 is a schematic view of the structure of a barrel of the present application, wherein FIG. 2(a) is a front view of the barrel, FIG. 2(b) is a bottom view of the barrel, and FIG. 2(c) is a perspective view of the structure of the barrel;

FIG. 3 is a schematic view of the structure of a plunger of the present application, wherein FIG. 3(a) is a front view of the plunger, FIG. 3(b) is a bottom view of the plunger, FIG. 3(c) is a sectional view of the plunger taken along line A-A, FIG. 3(d) is a sectional view of the plunger taken along line B-B, and FIG. 3(e) is a sectional view of the plunger taken along line C-C;

FIG. 6 is a schematic view of the structure of a thread conical connector of the present application, wherein FIG. 6(a) is a front view of the thread conical connector, FIG. 6(b) is a top view of the thread conical connector, and FIG. 6(c) is a perspective view of the thread conical connector;

FIG. 7 is a schematic view of the structure of a sealing ring of the present application, wherein FIG. 7(a) is a front view of the sealing ring, and FIG. 7(b) is a top view of the sealing ring;

FIG. 8 is a schematic view of the structure of a transition part of the present application, wherein FIG. 8(a) is a front view of the transition part, FIG. 8(b) is a bottom view of the transition part, and FIG. 8(c) is a perspective view of the transition part;

FIG. 9 is a schematic view of the structure of a hollow wedge of the present application, wherein FIG. 9(a) is a front view of the hollow wedge, FIG. 9(b) is a top view of the hollow wedge, and FIG. 9(c) is a perspective view of the hollow wedge;

In FIG. 1:
| | |
|---|---|
| 1. barrel; | 2. plunger; |
| 3. piston; | 4. thread conical connector; |
| 5. sealing ring; | 6. transition part; |
| 7. hollow wedge; | 9. syringe needle; |
| 10. protective cap; | 11. first annular flange; |
| 12. second annular flange; | 13. retaining annular groove; |
| 14. annular protruding portion; | 21. first retaining member; |
| 22. second retaining member; | 23. reinforcing rib; |
| 24. fragile portion; | 25. first tapered boss; |
| 26. second tapered boss; | 27. plunger pushing portion; |
| 28. slip-resistant rib; | |

In FIG. 2:
| | |
|---|---|
| | 15. strip inwardly protruding rib; |

In FIG. 4:
| | |
|---|---|
| | 8. conical connector assembly; |

In FIG. 6:
| | |
|---|---|
| 41. upper portion of the thread conical connector; | 411. conical connector hole; |
| 412. elastic retaining teeth; | 413. strip outwardly protruding rib; |
| 42. lower portion of the thread conical connector; | 421. annular inward flange; |

In FIG. 8:
| | |
|---|---|
| 61. outer connecting body; | 62. inner connecting body; |
| 621. annular groove; | 63. annular recess; |
| 64. blade; | 641. groove; |
| 642. small inwardly protruding portion; | 643. big inwardly protruding portion; |

In FIG. 9:
| | |
|---|---|
| 71. hollow cylinder; | 711. annular groove; |
| 72. elastic retaining teeth; | 73. inclined step. |

DETAILED DESCRIPTION

The present application is further described in conjunction with the drawings and embodiments.

As shown in FIGS. 1 to 9, the present application provides an easily assembled and highly safe self-destructive syringe.

Figure 1:
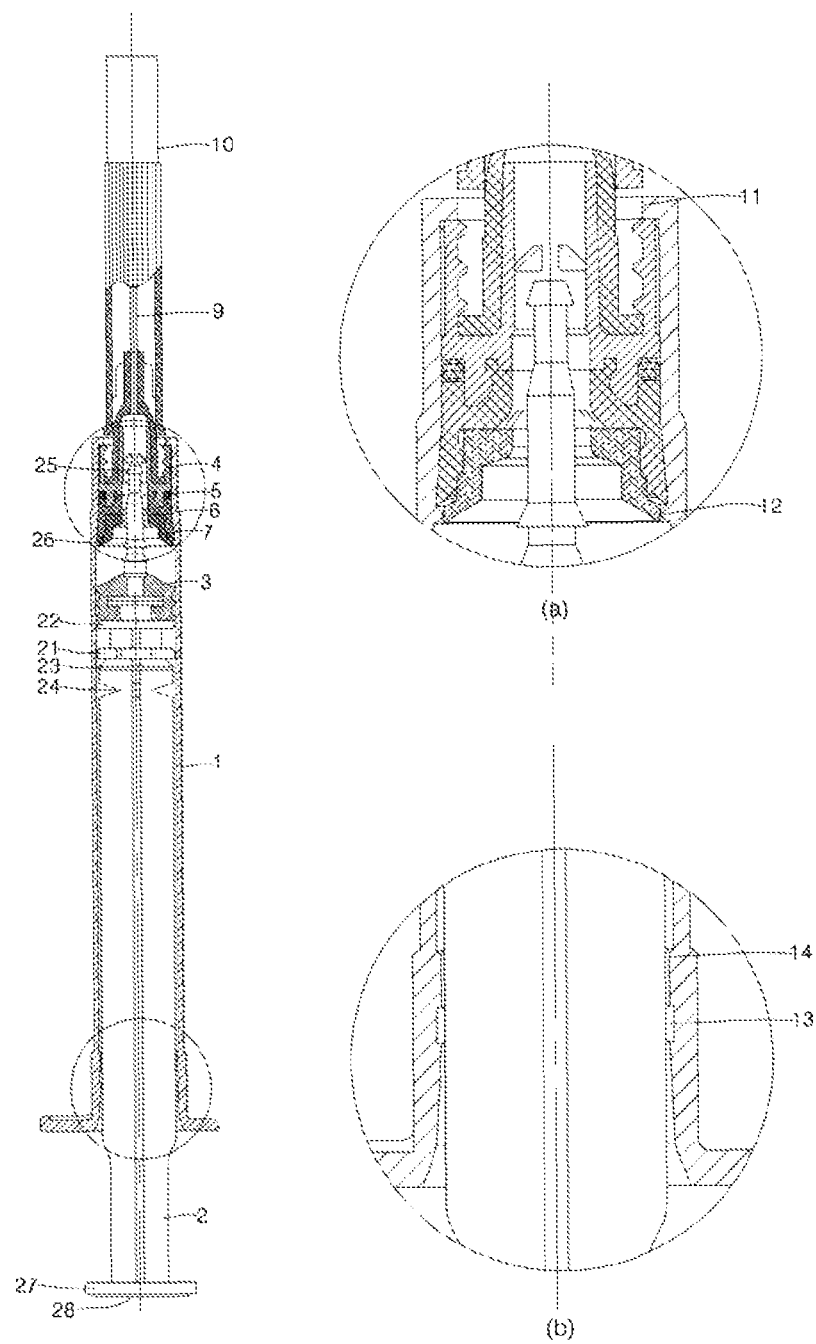
FIG. 1 is a schematic view of the planar structure of the present application (before use), wherein FIGS. 1(a) and (b) are partial enlarged views of FIG. 1.
Figure 2:
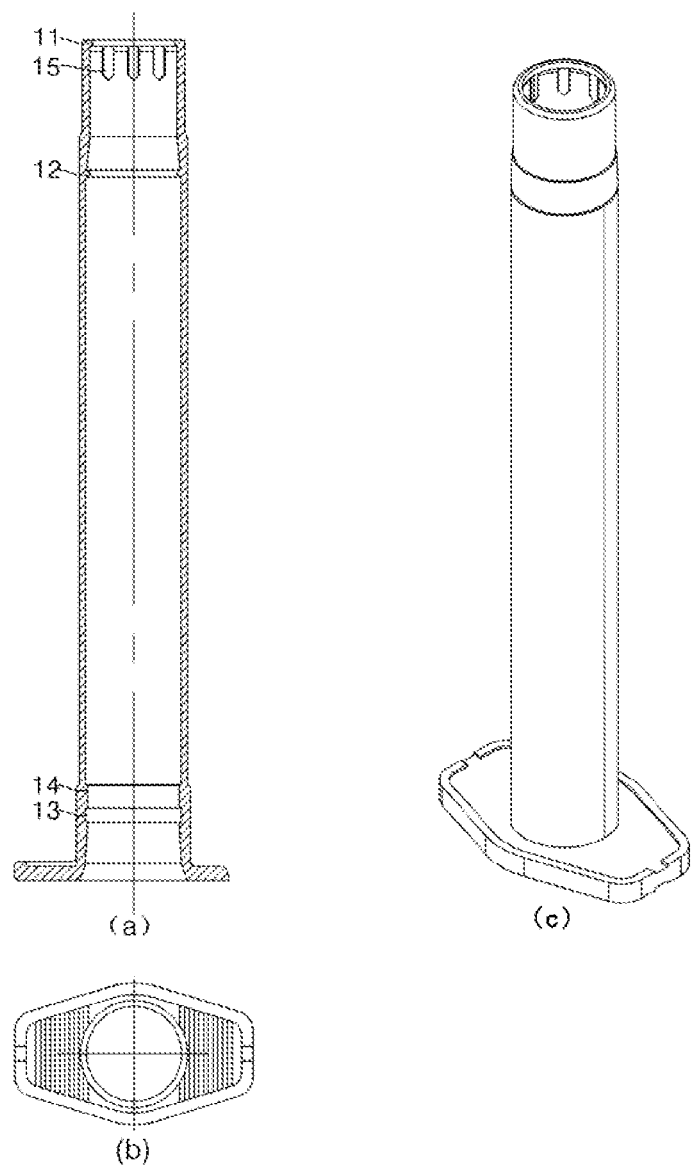
Figure 3:
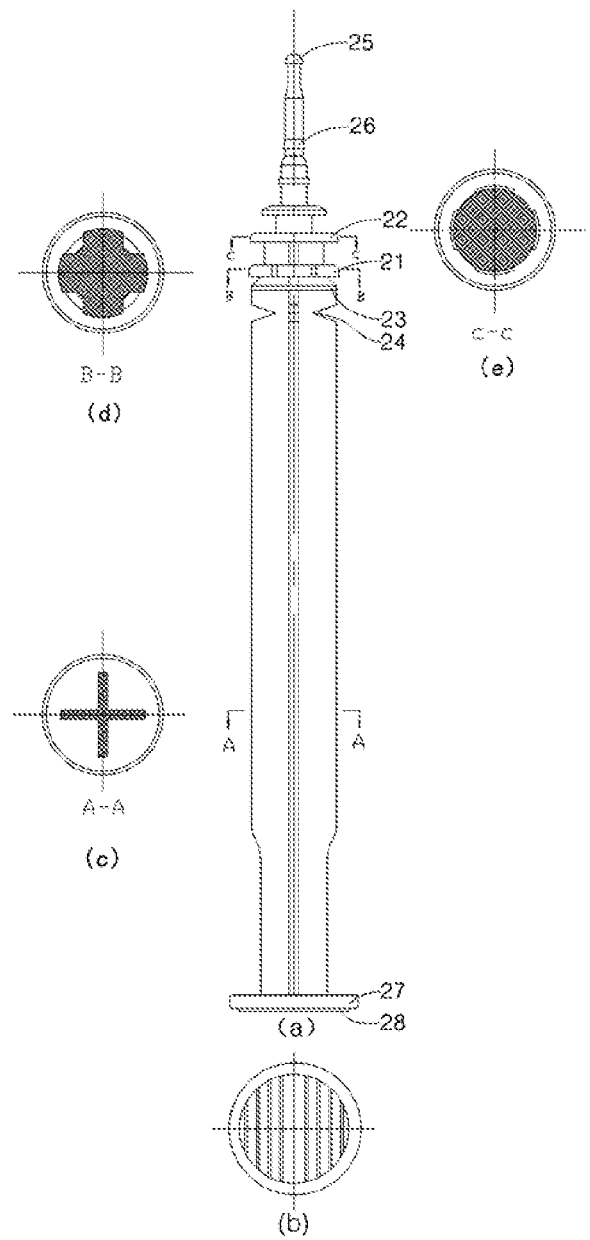
Figure 4:
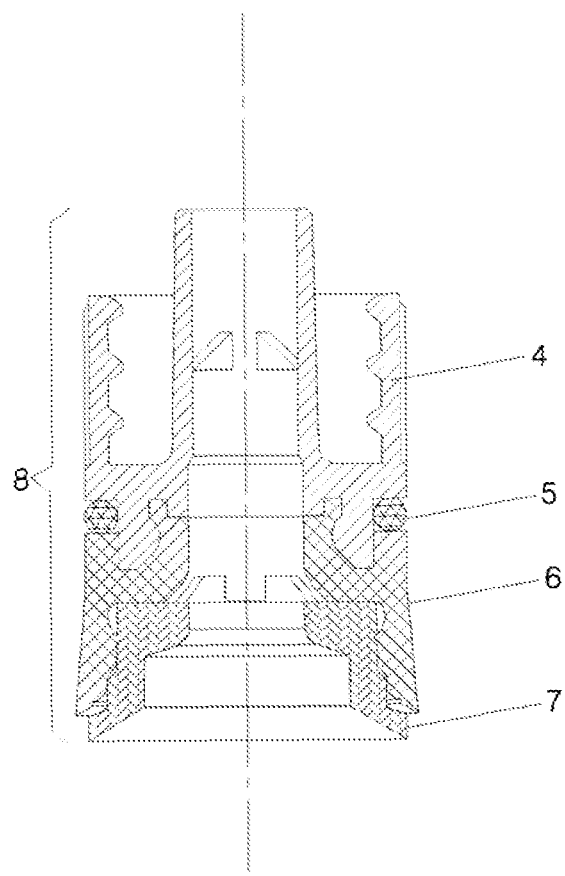
FIG. 4 is a schematic view of the structure of a conical connector assembly of the present application.
Figure 5:
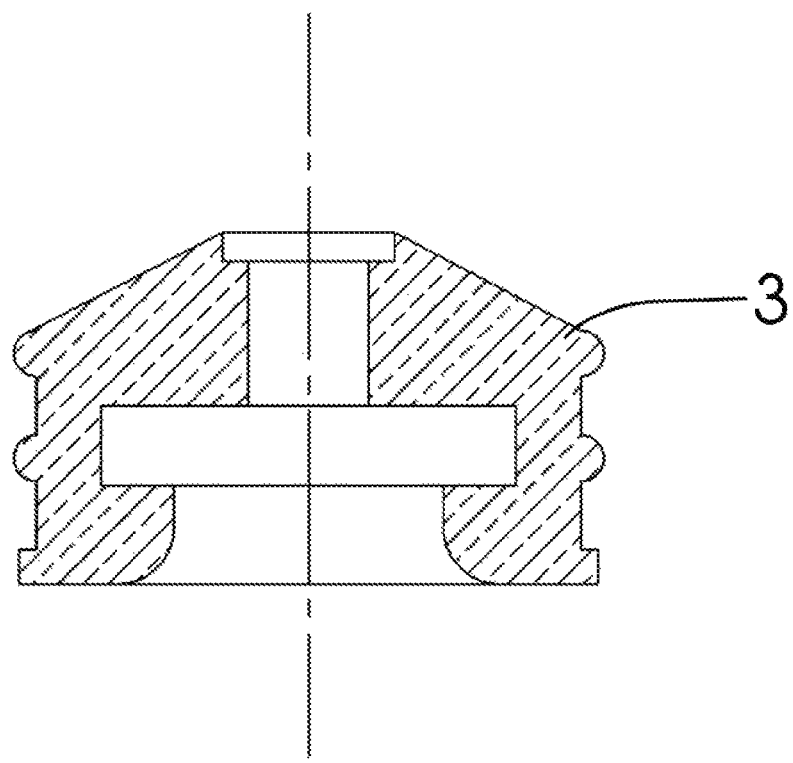
FIG. 5 is a schematic view of the structure of a piston of the present application.
Figure 6:
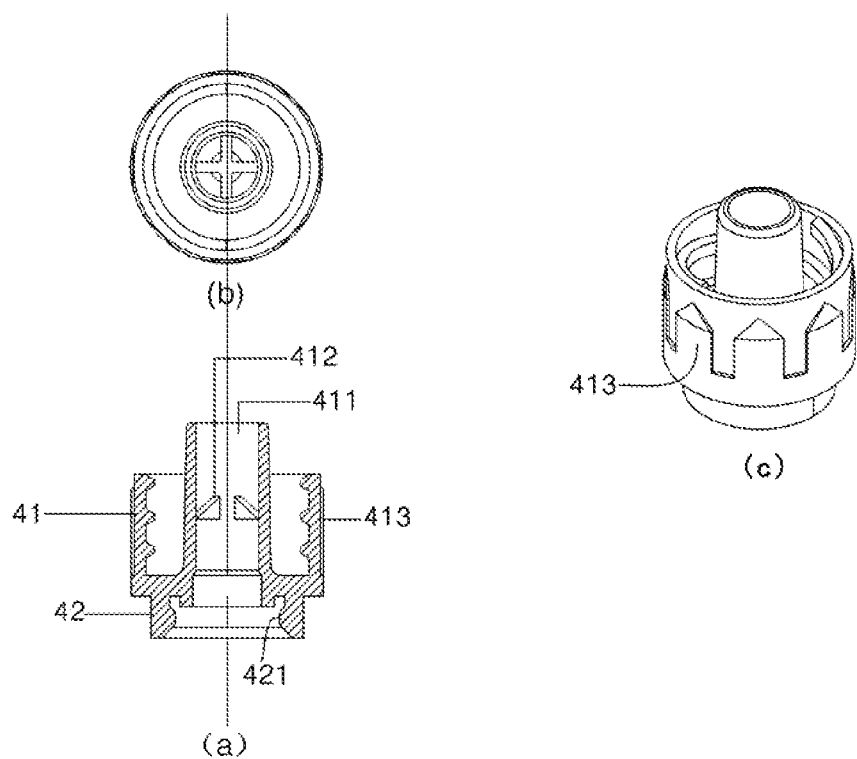
Figure 7:
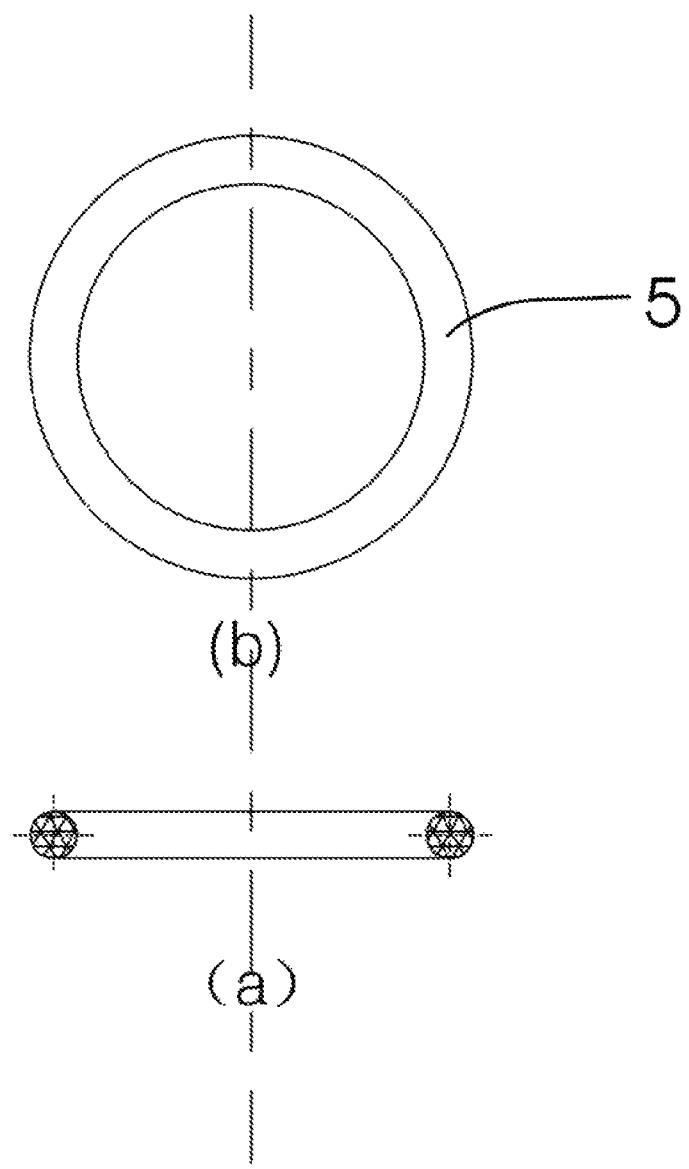
Figure 8:
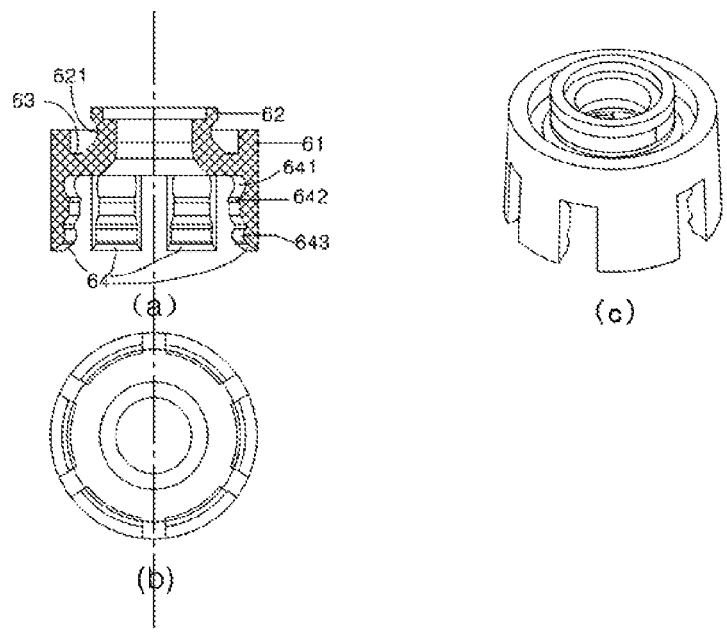
Figure 9:
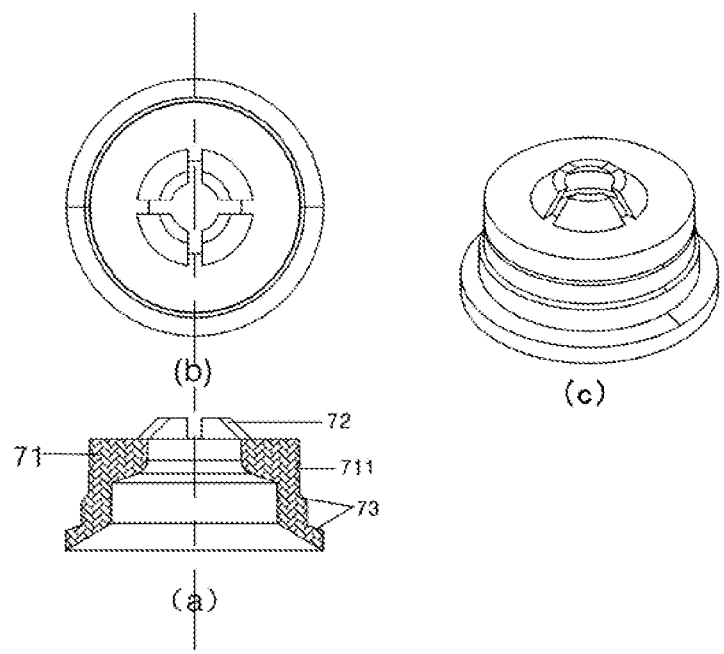
Figure 10:
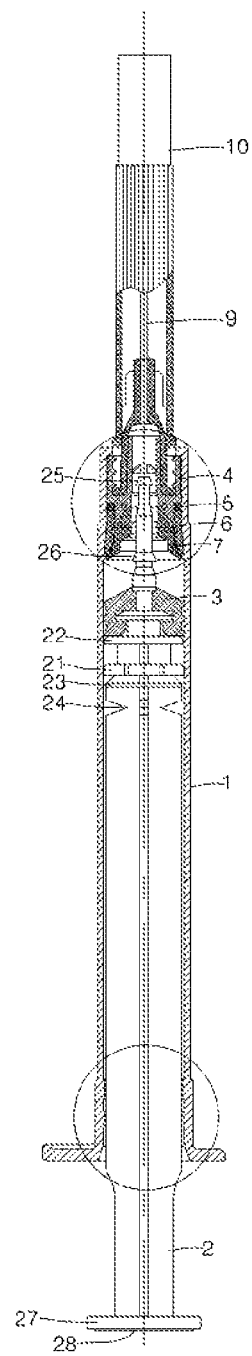
FIG. 10 is a schematic view of a first using state of the present application, with the protective cap being removed.
Figure 11:
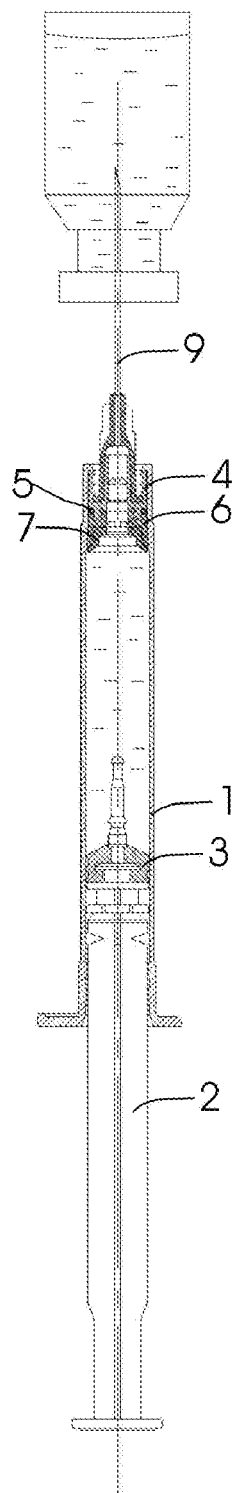
FIG. 11 is a schematic view of a second using state of the present application, showing absorbing the liquid medicine.
Figure 12:
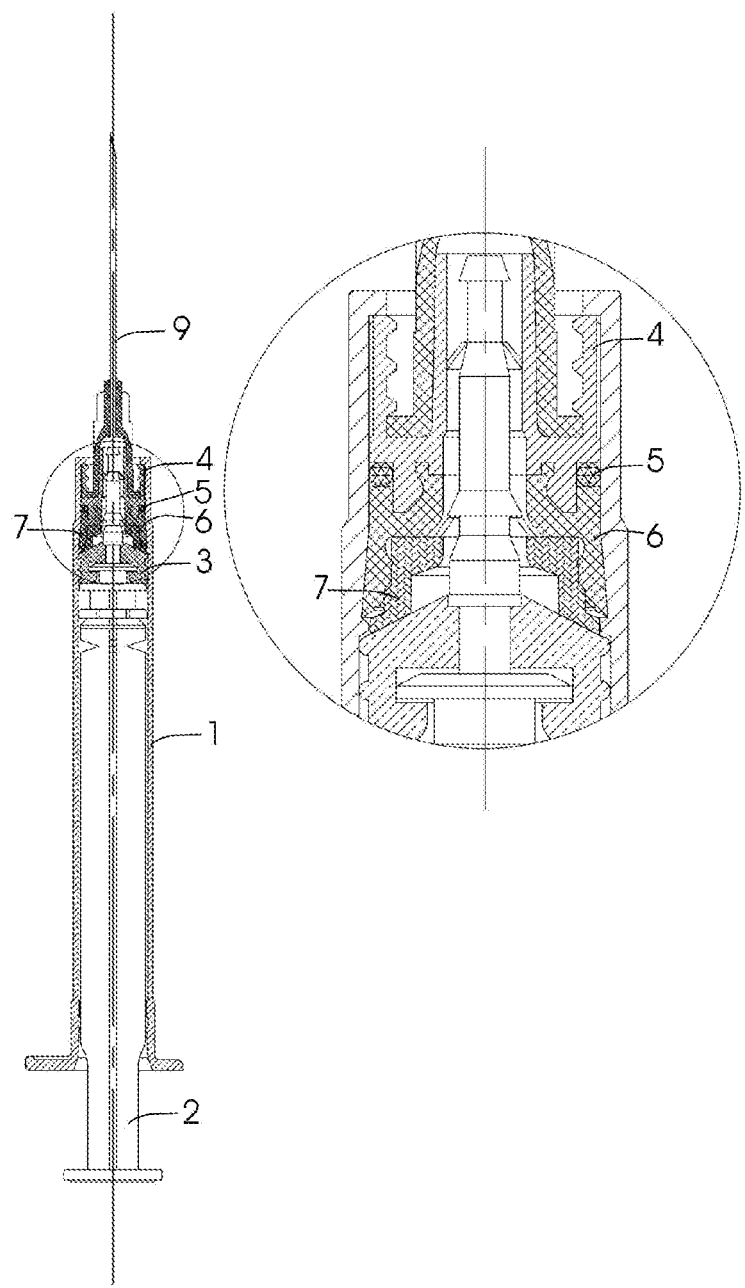
FIG. 12 is a schematic view of a third using state of the present application, when the injection is finished, wherein a right side of FIG. 12 is a partial enlarged view of the conical connector.
Figure 13:
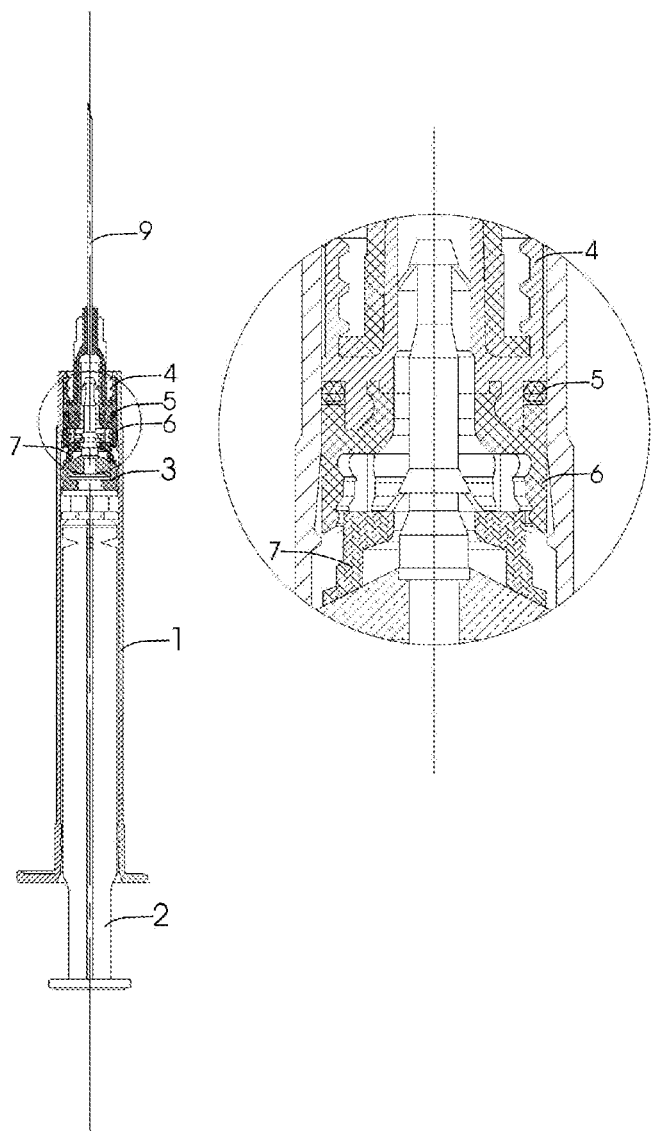
FIG. 13 is a schematic view of a fourth using state of the present application, with the plunger being pulled back, wherein a right side of FIG. 13 is a partial enlarged view of the conical connector, and the hollow wedge is pulled downwardly by a second tapered boss such that the transition part returns to its original state and is no longer restricted by the second annular flange.
Figure 14:
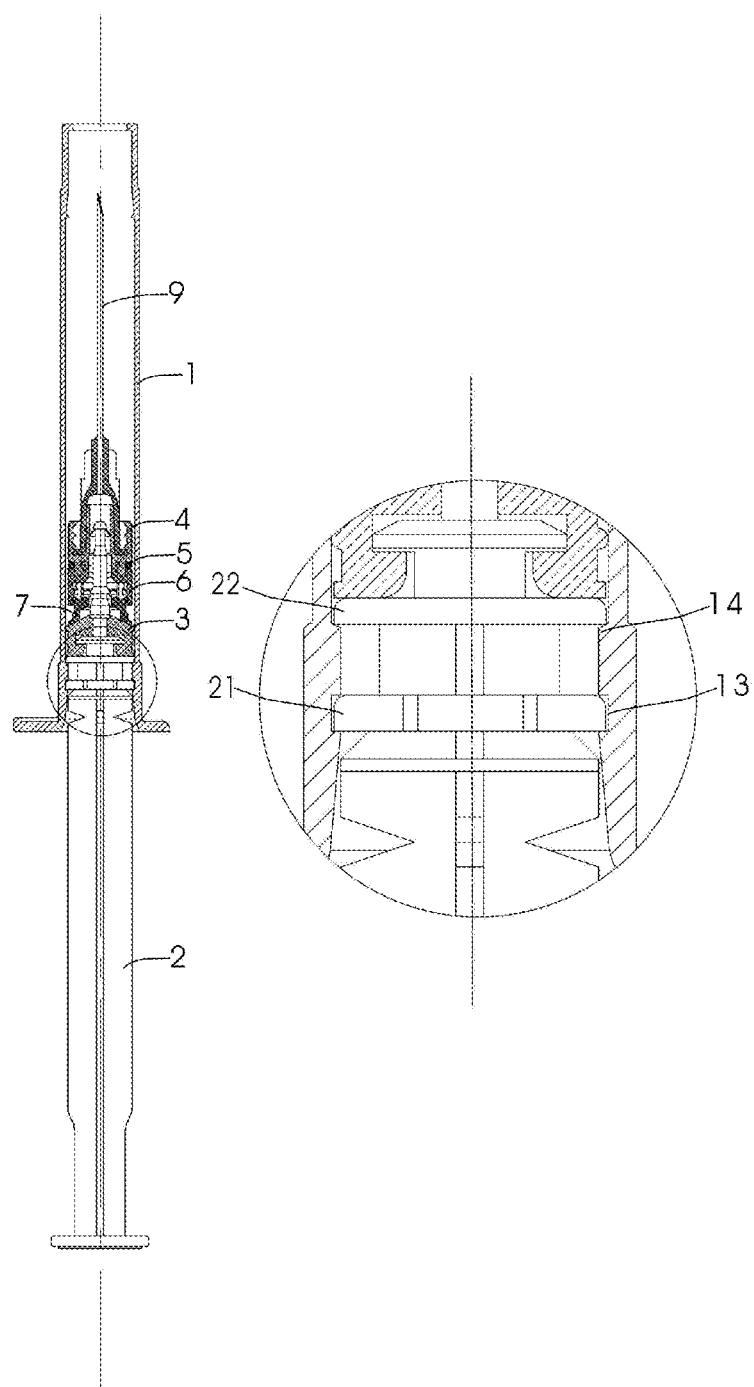
FIG. 14 is a schematic view of a fifth using state of the present application, wherein the plunger is pulled back until a retaining member of the plunger slides into an annular groove in an internal wall of a rear end of the barrel and the needle is retracted into the barrel, wherein a right side of FIG. 14 is a partial enlarged view of a tail portion of the barrel.
Figure 15:
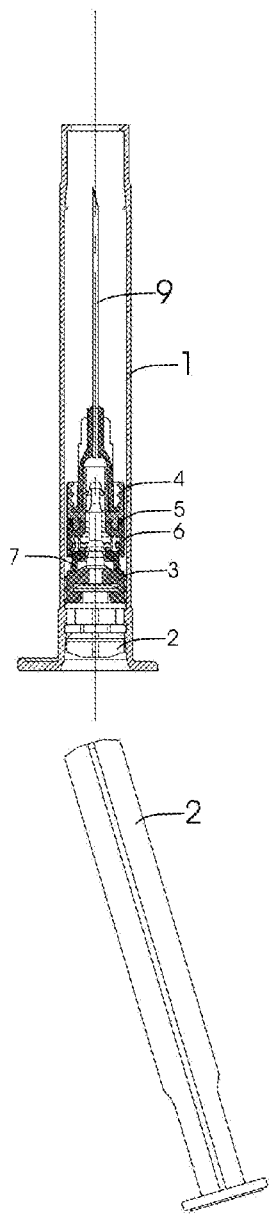
FIG. 15 is a schematic view of a fifth using state of the present application, with the plunger being broken.

As shown in FIG. 1, the easily assembled and highly safe self-destructive syringe includes a barrel 1, a plunger 2, a piston 3, a conical connector assembly 8, a syringe needle 9 and a protective cap 10. The syringe needle 9 is mounted in the conical connector assembly 8; the protective cap 10 is mounted above the syringe needle 9 to cover the syringe needle 9 and is movably connected to a needle seat of the syringe needle 9; the conical connector assembly 8 is mounted in an inner cavity of a front end of the barrel 1; the piston 3 is mounted on the plunger 2; a main body portion of the plunger 2 is mounted in the barrel 1, and a front end of the plunger 2 is inserted into the conical connector assembly 8 during the injection operation and then can drive the syringe needle 9 mounted on the conical connector assembly 8 to retract into the barrel 1 together. As shown in FIG. 4, the conical connector assembly 8 includes a thread conical connector 4, a sealing ring 5 (as shown in FIG. 7), a transition part 6 and a hollow wedge 7. As shown in FIG. 2, a first annular flange 11 is provided on an inner wall at an end surface of a head portion of the barrel 1, and a second annular flange 12 is provided on the inner wall below the first annular flange 11; a retaining annular groove 13 and an annular protruding portion 14 are provided on the inner wall of a rear end of the barrel 1; several longitudinal strip inwardly protruding ribs 15 are distributed uniformly on the inner wall of the barrel 1 below the first annular flange 11, all the strip inwardly protruding ribs 15 are starting at a same circumference at a root portion of a bottom surface of the first annular flange 11 and have the same length, and an inwardly protruding height of the inwardly protruding ribs 15 is lower than an inwardly protruding height of the first annular flange 11. A first retaining member 21 corresponding to the retaining annular groove 13 at the rear end of the barrel 1 and a second retaining member 22 corresponding to the annular protruding portion 14 at the rear end of the barrel 1 are provided on the plunger 2, and the first retaining member 21 consists of four arc sheets provided on a same circumference (the number of the arc sheets is not limited to four, however there should be at least two arc sheets). A thickness side of the first retaining member 21 is tangent to a circumference of a bottom surface of the first retaining member 21, and forms a chamfer angle with a circumference of a top surface of the first retaining member 21, such that the first retaining member 21 can smoothly pass through the retaining annular groove 13 in the inner wall of the rear end of the barrel 1 when the plunger 2 is moving forward in the inner cavity of the barrel 1, but can not pass through the retaining annular groove 13 when the plunger 2 is moving backward. The second retaining member 22 is an integral circle retaining member coaxial with the plunger 2, a circumference diameter of the second retaining member 22 is slightly less than a circumference diameter of the first retaining member 21 and is slightly larger than a diameter of the inner cavity of the barrel 1 at the annular protruding portion 14, and a thickness side of the second retaining member 22 also is tangent to a circumference of a bottom surface of the second retaining member 22, and forms a chamfer angle with a circumference of a top surface of the second retaining member 22. A reinforcing rib 23 is provided on the plunger below the first retaining member 21, a fragile portion 24 is provided on the plunger below the reinforcing rib 23, a first tapered boss 25 and a second tapered boss 26 are provided at the head portion of the plunger 2 sequentially along an axis, and a circumference diameter of a bottom surface of the first tapered boss 25 is less than a circumference diameter of a bottom surface of the second tapered boss 26. As shown in FIG. 3, a slip-resistant rib 28 is provided on a bottom surface of a pushing portion 27 of the plunger 2. As shown in FIGS. 1 and 5, the piston 3 is hollow, and the head portion of the plunger 2 passes through the piston 3 so as to mount the piston 3 at the front end of the plunger 2. As shown in FIG. 6, an upper portion 41 of the thread conical connector 4 is a standard Luer locking conical connector which can cooperate with various standard syringe needles; four elastic retaining teeth 412 are provided on a wall surface of an inner cavity of a conical connector hole 411 along a same circumference (the number of the elastic retaining teeth is not limited to four, however there should be at least two elastic retaining teeth); several longitudinal strip outwardly protruding ribs 413 are distributed uniformly on an outer surface of the upper portion 41 of the thread conical connector 4, and all the strip outwardly protruding ribs 413 are starting at a same circumference and have the same length; an outwardly protruding height of the strip outwardly protruding ribs 413 of the thread conical connector 4 is equal to an inwardly protruding height of the strip inwardly protruding ribs 15 of the barrel 1; an end portion of the upper portion 41 of the thread conical connector 4 has an outer diameter larger than a diameter of the inner cavity of the barrel 1 at the first annular flange 11, and has an inner diameter equal to or less than a diameter of the inner cavity of the barrel 1 at the first annular flange 11; and, the lower portion 42 of the thread conical connector is a hollow cylinder, and an annular inward flange 421 is provided on a wall surface of an inner cavity of the lower portion 42 of the thread conical connector 4. The transition part 6 has a hollow structure, an outer connecting body 61 and an inner connecting body 62 are provided on an upper portion of the transition part 6, the inner connecting body 62 is hollow, an annular recess 63 is formed between the outer connecting body 61 and the inner connecting body 62, an annular groove 621 in communication with the recess 63 is provided on an outer wall surface of the inner connecting body 62. Six spaced identical blades 64 (the number of the blade is not limited to six, however there should be at least three blades), extending downward from an outer wall surface of the outer connecting body 61, are provided at a lower portion of the transition part 6 and are uniformly distributed on a same circumference, a bottom surface of each blade 64 is a sloping surface, and a groove 641 is provided in an inner wall surface of each blade 64 to form a fragile portion of the blade so as to facilitate the outward expanding of the blades being pushed. As shown in FIG. 8, a big inwardly protruding portion 643 corresponding to an inclined step of the hollow wedge and a small inwardly protruding portion 642 corresponding to an annular groove of the hollow wedge are provided on the inner wall surface of each blade 64, and the small inwardly protruding portions 642 are fitted in the annular groove 711 for preventing the shock during the product transportation. As shown in FIG. 9, the hollow wedge 7 has a hollow structure, an upper portion of the hollow wedge 7 is a hollow cylinder 71, four elastic retaining teeth 72 protruding inwardly and upwardly are uniformly distributed along a circumference at an inner cavity opening of an end surface of a head portion of the hollow cylinder 71, an annular groove 711 is provided on an outer wall surface of the cylinder 71, and two annular inclined steps 73 inclining outwardly and downwardly are provided on an outer side of a lower portion of the cylinder 71.

In specific implementation, it should be ensured that a circumference diameter of the bottom surface of the first tapered boss 25 is less than a diameter of a circle formed by a top inner wall of the elastic retaining teeth 72, in a natural state, at the head portion of the hollow wedge 7, and is larger than a diameter of a circle formed by a top inner wall of the elastic retaining teeth 412, in a natural state, in the inner cavity of the thread conical connector 4; and a circumference diameter of the bottom surface of the second tapered boss 26 at the head portion of the plunger 2 is larger than the diameter of the circle formed by the top inner wall of the elastic retaining teeth 72, in a natural state, at the head portion of the hollow wedge 7.

The assembly of the conical connector assembly 8 is as follow. The lower portion 42 of the thread conical connector 4 is extended into the upper portion of the transition part 6 to fit with the annular recess 63, and the thread conical connector 4 and the transition part 6 are connected via the snap-fit between the annular inward flange 421 and the annular groove 621; meanwhile a sealing ring 5 is mounted between the thread conical connector 4 and the transition part 6, the sealing ring 5 is pressed tightly to form an interference fit so as to ensure the sealing among the thread conical connector 4, the transition part 6 and the inner wall of the barrel 1. The hollow wedge 7 is mounted under the transition part 6, the inclined steps 73 at the lower portion of the hollow wedge 7 outwardly press the six blades 64 at the lower portion of the transition part 6 to be expanded outwardly, such that the thread conical connector 4, the sealing ring 5 and the transition part 6 are tightly restricted between the first annular flange 11 and the second annular flange 12 on the inner wall of the barrel 1. The outer wall surface of a tail portion of the hollow wedge 7 and the inner cavity, formed by the second annular flange 12 on the inner wall of the barrel 1, form an interference fit, and the small inwardly protruding portion 642 and the annular groove 711 are snap fitted to further improve the cooperation, thereby achieving the transportation shockproof function. Due to the mutual restriction between the strip outwardly protruding ribs 413, distributed uniformly on the outer wall surface of the thread conical connector 4, and the strip inwardly protruding ribs 15, on the inner wall of the barrel 1 below the first annular flange 11, the conical connector assembly can not rotate, and meanwhile the conical connector assembly and the inner wall of the barrel 1 form an interference fit via the sealing ring 5 so as to achieve the sealing.

Further, it should also be ensured that a distance from the bottom surface of the second tapered boss 26 at the head portion of the plunger 2 to the bottom surface of the first tapered boss 25 is larger than a distance from the top surface of the elastic retaining teeth 72 of the hollow wedge 7 to the top surface of the elastic retaining teeth 412 in the inner cavity of the thread conical connector 4 in an assembled conical connector assembly, and the distance difference should be enough for the second tapered boss 26 to retract the hollow wedge 7 until the restriction to the blades 64 of the transition part 6 from the hollow wedge 7 is removed after the liquid medicine injection is finished. The first tapered boss 25 at the head portion of the plunger 2 corresponds to the elastic retaining teeth 412 in the thread conical connector 4, and the second tapered boss 26 corresponds to the elastic retaining teeth 72 at the head portion of the hollow wedge 7. When the plunger 2 moves forward in the inner cavity of the barrel 1, the bosses 25 and 26 and the elastic retaining teeth 72 and 412 form a forward tooth shape, thus the plunger 2 can pass through successfully, and when the plunger 2 is retracted, the bosses 25 and 26 and the elastic retaining teeth 72 and 412 form an reversed tooth shape.

When the injection of the predetermined liquid medicine in the syringe is finished, the head of the plunger 2 at the front end of the piston 3 is extended to the front of the elastic retaining teeth 412 in the inner cavity of the thread conical connector 4, so as to reduce the residual amount of the liquid medicine; meanwhile, when the liquid medicine injection is finished, the plunger 2 is retracted, firstly, the second tapered boss 26 hooks the elastic retaining teeth 72 at the head portion of the hollow wedge 7 to retract it, such that the restriction to the blades 64 of the transition part 6 from the hollow wedge 7 is removed; when the transition part 6 is not restricted by the hollow wedge 7, the outwardly expanded blades 64 of the transition part 6 return to the original state, thereby breaking away from the restriction from the second annular flange 12 on the inner wall of the barrel 1; meanwhile the first tapered boss 25 at the head portion of the plunger 2 hooks the elastic retaining teeth 412 in the inner cavity of the thread conical connector 4 and pulls back the conical connector assembly 8 so as to retract the syringe needle into the barrel 1, until the first retaining member 21 of the plunger 2 slides into the retaining annular groove 13 on the inner wall of the rear end of the barrel 1; meanwhile the second retaining member 22 is resisted by the annular protruding portion 14 on the inner wall of the rear end of the barrel 1, such that the retraction-stopping force on the plunger 2 becomes larger, in this situation when pulling hard the plunger 2, the plunger 2 may be broken due to the fragile portion 24 on the plunger 2, thereby achieving the self-destruction function of the syringe and the security protection function of the syringe needle.

The using process of the present application is shown in FIGS. 10 to 15.

The portions that are not referred to in the present application are the same as that in the prior art or can be implemented by using the prior art.

What is claimed is:

1. A self-destructive syringe, comprising:
   a barrel;
   a plunger;
   a piston;
   a conical connector assembly;
   a syringe needle; and
   a protective cap;
   wherein:
      the syringe needle has a needle seat which is mounted in the conical connector assembly;
      the protective cap is mounted above the syringe needle to cover the syringe needle and is movably connected to the needle seat of the syringe needle;
      the conical connector assembly is mounted in an inner cavity of a front end of the barrel;
      the piston is mounted at a front end of the plunger;
      a main body portion of the plunger is mounted in the barrel;
      the front end of the plunger is configured to insert into the conical connector assembly during an injection operation and drive the syringe needle mounted on the conical connector assembly to retract into the barrel;
      the conical connector assembly comprises:
         a thread conical connector having an upper portion engaged with the needle seat of the syringe needle;
         a sealing ring;
         a transition part; and
         a hollow wedge;
         wherein:
            a lower portion of the thread conical connector is configured to be inserted into an annular groove and an annular recess of the transition part;
            the sealing ring is press fitted among joint surfaces of the thread conical connector, the transition part and an inner cavity wall surface of the front end of the barrel, and
            the hollow wedge is insertedly mounted in the transition part and has two annular inclined steps configured to expand spaced blades at a lower part of the transition part, to locate the conical connector assembly in the inner cavity of the front end of the barrel.

2. The syringe according to claim 1, wherein:
   the hollow wedge comprises a hollow structure;
   an upper portion of the hollow wedge is a hollow cylinder;
   at least two elastic retaining teeth protruding inwardly and upwardly are uniformly distributed along a circumference at an inner cavity opening of an end surface of a head portion of the hollow cylinder;
   an annular groove is provided on an outer wall surface of the cylinder; and
   the two annular inclined steps inclining outwardly and downwardly are provided on an outer side of a lower portion of the cylinder.

3. The syringe according to claim 2, wherein:
the transition part is of a hollow structure;
an outer connecting body and an inner connecting body are provided on an upper portion of the transition part;
the inner connecting body is hollow;
the annular recess is formed between the outer connecting body and the inner connecting body;
the annular groove of the transition part in communication with the annular recess is provided on an outer wall surface of the inner connecting body;
a plurality of spaced identical blades, extending downward from an outer wall surface of the outer connecting body, are provided at a lower portion of the transition part and are uniformly distributed on a same circumference;
a bottom surface of each blade is a sloping surface, a groove is provided in an inner wall surface of each blade to form a fragile portion of the blade so as to facilitate the outward expanding of the blades being pushed;
a first inwardly protruding portion corresponding to the two annular inclined steps of the hollow wedge and a second inwardly protruding portion corresponding to the annular groove of the hollow wedge are provided in the inner wall surface of each blade; and
the second inwardly protruding portion is fitted in the annular groove of the hollow wedge for preventing the shock during the product transportation.

4. The syringe according to claim 3, wherein:
a first annular flange is provided on an inner wall at an end surface of a head portion of the barrel and is configured to restrict the assembled conical connector assembly from being pushed forward;
a second annular flange is provided on the inner wall below the first annular flange and is configured to restrict the assembled conical connector assembly from being retracted;
a retaining annular groove and an annular protruding portion are provided on the inner wall of a rear end of the barrel;
a plurality of longitudinal strip shaped inwardly protruding ribs are distributed uniformly on the inner wall of the barrel below the first annular flanges; and
an inwardly protruding height of the inwardly protruding ribs is lower than an inwardly protruding height of the first annular flange.

5. The syringe according to claim 4, wherein:
a first retaining member corresponding to the retaining annular groove at the rear end of the barrel and a second retaining member corresponding to the annular protruding portion at the rear end of the barrel are provided on the plunger;
the first retaining member comprises at least two arc sheets provided on a same circumference;
a thickness side of the first retaining member is tangent to a circumference of a bottom surface of the first retaining member, and forms a chamfer angle with a circumference of a top surface of the first retaining member, to allow the first retaining member to pass through the retaining annular groove in the inner wall of the rear end of the barrel when the plunger is moving forward in an inner cavity of the barrel, and prevent the first retaining member to pass through the retaining annular groove when the plunger is moving backward;
the second retaining member is an integral circle retaining member coaxial with the plunger, a circumference diameter of the second retaining member is slightly smaller than a circumference diameter of the first retaining member and is slightly greater than a diameter of the inner cavity of the barrel at the annular protruding portion, and a thickness side of the second retaining member also is tangent to a circumference of a bottom surface of the second retaining member, and forms a chamfer angle with a circumference of a top surface of the second retaining member;
a reinforcing rib is provided on the plunger below the first retaining member, a fragile portion is provided on the plunger below the reinforcing rib, a first tapered boss and a second tapered boss are provided at a head portion of the plunger sequentially along an axis of the plunger, a circumference diameter of a bottom surface of the first tapered boss is smaller than a circumference diameter of a bottom surface of the second tapered boss; and
a bottom of the plunger is provided with a pushing portion, and a slip-resistant rib is provided on a bottom surface of the pushing portion of the plunger.

6. The syringe according to claim 5, wherein:
the upper portion of the thread conical connector is a Luer locking conical connector which can cooperate with various standard syringe needles;
the thread conical connector comprises a conical connector hole configured to allow the front end of the plunger to be inserted therein, and at least two elastic retaining teeth are provided on a wall surface of an inner cavity of the conical connector hole along a same circumference, a plurality of strip-shaped outwardly protruding ribs are distributed uniformly on an outer surface of the upper portion of the thread conical connector, an end portion of the upper portion of the thread conical connector has an outer diameter greater than a diameter of the inner cavity of the barrel at the first annular flange, and has an inner diameter equal to or smaller than a diameter of the inner cavity of the barrel at the first annular flange;
the lower portion of the thread conical connector is a hollow cylinder, and an annular inward flange is provided on a wall surface of an inner cavity of the lower portion of the thread conical connector.

7. The syringe according to claim 6, wherein:
the circumference diameter of the bottom surface of the first tapered boss at the head portion of the plunger is smaller than a diameter of a circle formed by a top inner wall of elastic retaining teeth, in a natural state, at the head portion of the hollow wedge, and is greater than a diameter of a circle formed by a top inner wall of elastic retaining teeth, in a natural state, in the inner cavity of the thread conical connector; and
the circumference diameter of the bottom surface of the second tapered boss at the head portion of the plunger is greater than the diameter of the circle formed by the top inner wall of the elastic retaining teeth, in the natural state, at the head portion of the hollow wedge.

8. The syringe according to claim 6, wherein:
the strip-shaped outwardly protruding ribs, distributed uniformly on the outer wall surface of the thread conical connector, cooperate with the strip-shaped inwardly protruding ribs, provided on the inner wall of the barrel below the first annular flange, to ensure that the conical connector assembly cannot rotate; and
the conical connector assembly and the inner wall of the barrel form an interference fit via the sealing ring to achieve the sealing.

9. The syringe according to claim 6, wherein:
a distance from the bottom surface of the second tapered boss at the head portion of the plunger to the bottom surface of the first tapered boss is greater than a distance from a top surface of the elastic retaining teeth of the hollow wedge to a top surface of the elastic retaining teeth in the inner cavity of the thread conical connector in an assembled conical connector assembly, and the distance difference is enough for the second tapered boss to retract the hollow wedge until the restriction to the blades of the transition part from the hollow wedge is removed after a liquid medicine injection is finished;
the first tapered boss at the head portion of the plunger corresponds to the elastic retaining teeth in the thread conical connector, and the second tapered boss corresponds to the elastic retaining teeth at the head portion of the hollow wedge;
when the plunger moves forward in the inner cavity of the barrel, the elastic retaining teeth of the thread conical connector forms a forward tooth shape with respect to the first tapered boss, and the elastic retaining teeth of the hollow wedge forms a forward tooth shape with respect to the second tapered boss, to allow the first tapered boss and the second tapered boss of the plunger to respectively pass through the elastic retaining teeth of the thread conical connector and the elastic retaining teeth of the hollow wedge, and then when the plunger is retracted, the elastic retaining teeth of the thread conical connector forms a reversed tooth shape with respect to the first tapered boss, and the elastic retaining teeth of the hollow wedge forms a reversed tooth shape with respect to the second tapered boss, to prevent the first tapered boss and the second tapered boss of the plunger to respectively pass through the elastic retaining teeth of the thread conical connector and the elastic retaining teeth of the hollow wedge.

10. The syringe according to claim 6, wherein:
when an injection of predetermined liquid medicine in the syringe is finished, the head portion of the plunger at the front end of the piston is extended to the front of the elastic retaining teeth in the inner cavity of the thread conical connector, to reduce a residual amount of the liquid medicine; meanwhile, when the liquid medicine injection is finished, the plunger is retracted, firstly, the second tapered boss hooks the elastic retaining teeth at the head portion of the hollow wedge to retract the hollow wedge, to remove the restriction of the hollow wedge to the blades of the transition part; and when the transition part is not restricted by the hollow wedge, the outwardly expanded blades of the transition part return to an original state, to be disengaged from the restriction of the second annular flange on the inner wall of the barrel;
the first tapered boss at the head portion of the plunger hooks the elastic retaining teeth in the inner cavity of the thread conical connector and pulls back the conical connector assembly to retract the syringe needle into the barrel, until the first retaining member of the plunger slides into the retaining annular groove on the inner wall of the rear end of the barrel;
the second retaining member is resisted by the annular protruding portion on the inner wall of the rear end of the barrel, to allow a retraction-stopping force on the plunger to become larger, and then when the plunger is further pulled, the plunger is broken due to the fragile portion provided on the plunger, to achieve a self-destruction function of the syringe and a security protection function of the syringe needle.

* * * * *